United States Patent [19]

Abou-Gharbia et al.

[11] Patent Number: 5,183,819
[45] Date of Patent: Feb. 2, 1993

[54] USE OF FUSED BICYCLIC IMIDES IN THE TREATMENT OF VARIOUS CNS DISORDERS

[75] Inventors: Magid A. M. Abou-Gharbia, Delaware; John A. Moyer, Bucks, both of Pa.

[73] Assignee: American Home Products Corporation, New York, N.Y.

[21] Appl. No.: 881,443

[22] Filed: May 11, 1992

[51] Int. Cl.[5] ........................................... A61K 31/495
[52] U.S. Cl. ..................................... 514/255
[58] Field of Search .......................... 514/255

[56] References Cited

U.S. PATENT DOCUMENTS

| | | | |
|---|---|---|---|
| 4,797,488 | 1/1989 | Stack | 544/295 |
| 4,892,943 | 1/1990 | Abou-Gharbia | 540/575 |
| 4,895,848 | 1/1990 | Traber | 514/255 |
| 5,010,078 | 4/1991 | Abou-Gharbia | 514/252 |

FOREIGN PATENT DOCUMENTS 0356997 8/1989 European Pat. Off. .

OTHER PUBLICATIONS

Abou-Gharbia et al., J. Med. Chem. 31, 1382-92 (1988).
White et al., Pharmacology Biochemistry and Behavior 39, 729-736 (1988).
Olivier et al., Drugs of the Future 11(6), 473 94 (1986).
Collins and Myers, Alcohol 4, 49-56 (1987).
Wauguier and Dugovie, Ann. N.Y. Acad. Sci. 600, 447-459 (1990).

Primary Examiner—S. J. Friedman
Attorney, Agent, or Firm—Robert F. Boswell, Jr.

[57] ABSTRACT

The invention relates to a method of treating alcoholism, sleep disorders or behavioral symptoms of Alzheimer's disease which comprises administration of bridged 2-(4-arylpiperazin-1-ylalkyl)-hexahydroisoindol-1,3-dione derivatives to a warm-blooded animal in need thereof.

2 Claims, No Drawings

USE OF FUSED BICYCLIC IMIDES IN THE TREATMENT OF VARIOUS CNS DISORDERS

BACKGROUND OF THE INVENTION

Some members of a class of compounds containing the 1-(2-pyrimidinyl)-4-alkylenepiperazine moiety as represented by the formula:

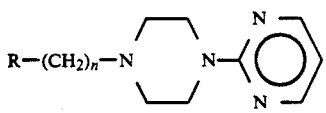

where n is 2 to 6 and R is

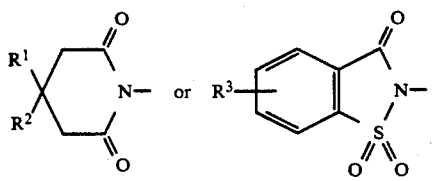

and $R^1$, $R^2$ and $R^3$ are independently hydrogen or lower-alkyl, and exemplified by the compounds known as gepirone and ipsapirone, have been disclosed in U.S. Pat. No. 4,895,848 as being useful in the treatment of alcoholism. The related compound buspirone has been shown to lower the preference for alcohol in monkeys with a preference for alcohol. The three compounds buspirone, gepirone and ipsapirone are known serotonin receptor modulators, especially at the serotonin $5HT_{1A}$ receptor subtype.

The European patent application EP 0356997A2 discloses the use of azapirone compounds in the treatment of substance addiction comprising over-eating, habitual use of tobacco, marijuana, cocaine, opiates, amphetamines, methylphenidate and related designer drugs and other recreational drugs. These compounds have been previously disclosed as psychotropic agents with useful anxiolytic properties and are encompassed by the formula:

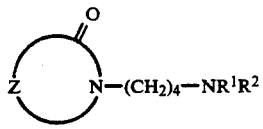

wherein: Z is selected from the group consisting of

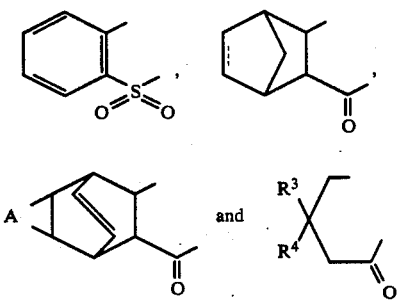

with $R^3$ and $R^4$ being independently selected from $C_1$-$C_4$ alkyl and hydrogen or $R^3$ and $R^4$ can be taken together as a butanediyl or pentanediyl chain thereby forming a spiro ring system. The —$NR^1R^2$ group can be taken as the 1-(2-pyrimidinyl)piperazinyl moiety or $R^1$ is H and $R^2$ is the group

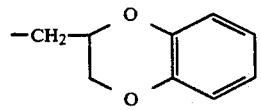

and A is selected from —$CH_2$—, —O—, —$CH_2CH_2$— and —CH=CH—.

The patent disclosing the compounds useful in treating substance addiction includes the compounds buspirone, gepirone, ipsapirone, and zalospirone (3a,4,4a,6a,-7a-hexahydro-2-[4-[4-(2-pyrimidinyl)-1-piperazinyl]-butyl]-4,7-ethano-1H-cyclobut[f]isoindole-1,3(2H)-dione). The latter compound is disclosed in our U.S. Pat. No. 4,892,943 and in J. Med. Chem. 31(7), 1382–92 (1988) as having antipsychotic/anxiolytic properties with a low liability for extrapyramidal side effects and is classified as a $5HT_{1A}$ modulator. Other N-[(4-arylpiperazin-1-yl)alkyl]bicyclicimides are disclosed in our U.S. Pat. No. 4,797,488 as antipsychotic/anxiolytic agents with low liability for extrapyramidal side effects.

DETAILED DESCRIPTION OF THE INVENTION

This invention is related to the use of compounds having the structure shown in Formula I below for the treatment of alcoholism, sleep disorders, and behavioral symptoms observed in patients having Alzheimer's disease.

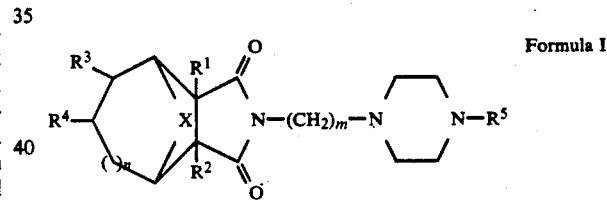

Formula I

Under Formula I, the following definitions apply:

$R^1$ and $R^2$ are H or $R^1$ and $R^2$ taken together forms a 3–5 membered carbocyclic ring;

$R^3$ and $R^4$ are H or $R^3$ and $R^4$ taken together form a 3–6 membered carbocyclic ring;

with a proviso that when $R^1$, $R^2$, $R^3$ and $R^4$ are other than hydrogen, n is other than 0;

X is lower alkylene, vinylene or O;

$R^5$ is unsubstituted or substituted phenyl, 2-pyridinyl, 2-pyrimidinyl, 2-pyrazinyl or 3-pyrazinyl where the substituents are selected from lower alkyl, lower alkoxy, halo, cyano, nitro and trifluoromethyl;

and the pharmaceutically acceptable salts thereof.

In the above description of Formula I, the term lower alkyl refers to moieties having 1–6 carbon atoms in a chain. The term lower alkoxy refers to —O—loweralkyl moieties having 1–6 carbon atoms in a chain. The term "alkylene" refers to moieties having 1–4 carbons in a chain. The term "vinylene" refers to the —CH=CH— group. The term halo means fluoro, chloro or bromo.

The term "pharmaceutically acceptable salts" refers to solvates, hydrates and acid addition salts wherein the acid is a pharmaceutically acceptable inorganic or organic acid such as hydrochloric, hydrobromic, sulfonic, sulfuric, phosphoric, nitric, fumaric, maleic, benzoic, ascorbic, pamoic, acetic, propionic, lactic, succinic, methanesulfonic, malic, citric, tartaric, mandelic, cinnamic, palmitic, itoconic, and benzensulfonic acid.

The compounds encompassed by Formula I have demonstrated activity at the serotonin 5-HT$_{1A}$ receptor subtype. Such serotonergic activity is believed to be involved in the control of compulsory behavior and sleep. These compounds demonstrated antiagression activity in an animal model. Such activity could be useful in controlling the symptoms of aggressive behavior in Alzheimer's disease patients.

Like buspirone, gepirone and ipsapirone, an invention compound where X is vinylene, $R^5$ and $R^6$ form a cyclobutene ring, n is 0, m is 4, $R^3$ and $R^4$ are H, and $R^7$ is 2-pyrimidinyl (zalospirone) has been shown to reduce aggression in isolation-induced aggressive mice without the debilitating (sedating) effects at the antiaggressive dose that are associated with a neuroleptic agent such as haloperidol [White, et al., Pharmacology Biochemistry & Behavior, 39, 729–736 (1991)]. The various paradigms used in evaluating antiaggressive agents are discussed in Drugs of the Future, 11(6), 473–494 (1986). The isolation-induced aggression paradigm is one of the most widely used aggression models in behavioral pharmacology. Serotonergic compounds which reduce aggression may be of value in treating agitation, aggression and other behavioral symptoms in patients diagnosed as having Alzheimer's disease. Thus the compounds encompassed by Formula I, based on similarities observed in standard pharmacological tests with other compounds, can be of value in treating the aggressive behavior observed in patients having Alzheimer's disease.

Serotonin is implicated in the induction and maintenance of sleep in the sleep-wake cycle. Sleep is the result of an integrated action of the central nervous system where neurons from different areas of the brain are involved in the patterns of the sleep cycle: slow wave sleep, paradoxical sleep, REM (rapid eye movement) sleep and wakefulness. Chemical compounds which act as agonists or antagonists at serotonin receptors in the brain can modify the sleep-wake pattern. The serotonin 5-HT$_{1A}$ agonists buspirone and 8-hydroxy-2-(di-n-propylamino)tetralin (8-OH-DPAT) increased wakefulness and reduced both slow wave sleep and paradoxical sleep following intravenous or subcutaneous administration in rats. Since a compound of this invention, zalospirone, is known to modulate the effects of serotonin at 5-HT$_{1A}$ receptor sites, the compounds of this invention would be expected to alter the sleep-wake pattern and thus have use in the treatment of sleep disorders.

PHARMACOLOGY

The following pharmacological procedures are employed to determine serotonin 5-HT$_{1A}$ receptor binding and antiaggressive activity.

1. Serotonin 5-HT$_{1A}$ Receptor Binding Assay

5-HT$_{1A}$ receptor affinity was measured in hippocampal rat brain tissue by using a modification of the method of Hall et al., J. Neurochem. 44, 1685 (1985). Several rats were decapitated and the brains were rapidly removed. Hippocampal tissue was dissected and homogenized on ice in 40 volumes of buffer A (50 mM Tris.HCl, pH 7.7) with a Polytron homogenizer at setting 5 for three 15-second bursts. The homogenate was then centrifuged at 48000 g for 10 min and the supernatant discarded. The pellet was resuspended in 40 volumes of the same buffer and incubated at 37° C. for 10 min to aid in the removal of endogenous serotonin. The homogenate was then centrifuged (as above) and the supernatant discarded. The pellet was then resuspended in 100 volumes of buffer B (50 mM Tris.HCl, pH 7.7 containing 0.5% ascorbate, 10 μM pargyline, and 4 mM CaCl$_2$) and sonicated. An aliquot was taken for protein determination by the Lowry method and the remainder stored frozen at −70° C. until used.

The homogenate (500 μL; 0.4–0.6 mg of protein/sample) was incubated with 100 μL (1.5–1.8 nM) [$^3$H]-8-hydroxy-2-(di-n-propylamino)tetralin (8-OH-DPAT) and various concentrations of test drug in a final volume of 2 mL of buffer B for 10 min at 37° C. At the end of the incubation, 3 mL of cold buffer A was added to each tube, and the contents were rapidly filtered through Whatman GF/B glass filters. The filters were then rapidly washed two times with 3 mL of the same buffer, placed in scintillation vials, and shaken for 15 min with 10 mL of Hydrofluor (National Diagnostics) scintillation cocktail. The vials were then counted in a Packard 460 CD scintillation counter.

Specific binding was defined at total binding less binding in the presence of 1 μM serotonin. Binding in the presence of various concentrations of test drug was expressed as a percent of specific binding when no drug was present. These results were then plotted as logit percent binding vs log concentration of test drug. Linear regression analysis then yields a straight line with 95% confidence limits from which an IC$_{50}$ can be inversely predicted. K$_i$ (inhibition constant) for the test drug was then calculated by the formula:

$$K_i = \frac{IC_{50}}{1 + [[H^3]8\text{-}OH\text{-}DPAT]/K_D}$$

The K$_D$ value for [$^3$H]-8-OH-DPAT binding in hippocampus was 1.8 nM.

2. Antiaggressive Behavior

Animals

Male CF-1 mice (16–20 g) were obtained from Charles River Breeding Laboratories, Kingston, NY. Animals were allowed to acclimate for at least 3 days after their arrival. Food and water were available ad lib. The animal colony was maintained at 22° C. with a 12-h light/dark cycle with lights on at 6 a.m.

Behavioral Testing

Antagonism of isolation-induced agression tests were conducted according to a modification of the method of Da Vanzo et al, Psychopharmacologia 9, 210–219 (1966) and McMillen et al., Naunyn Schmiedebergs Arch. Pharmacol. 335, 454–464 (1987). The mice were individually housed or group housed (6/cage) in self-cleaning cages (25×18×18 cm) for a period of 3 weeks. After the 3 week period of isolation, the individually housed (isolated) mice were trained to attack a group-housed (intruder) mouse. The cage containing the isolated mouse was removed from the cage rack and placed on a bench top covered with absorbent paper. After a 3 minute acclimation period, the isolated mouse was "bumped" into several times with the intruder mouse which was then released into the isolated mouse's home cage. After 3 minutes of exposure, the intruder mouse was removed and returned to its own cage. The isolated mice were trained on 5 successive days prior to their experimental use. The trained isolated mice were prescreened for aggressive behavior one day before the experiment. As in the training session, the intruder mouse was introduced into the isolated mouse's home cage for 3 minutes. The total fighting time (TFT) in seconds was recorded during the 3 minute test. Isolated mice fighting for more than 20 seconds were used for drug testing on the following day. On test day, test compound or vehicle was administered IP 60 minutes prior to aggression testing (N=5-25/dose). As in prescreening, the cage containing the isolated mouse was removed from the cage rack and placed on a bench top covered with absorbent paper. After a 3 minute acclimation period, the isolated mouse was "bumped" into several times with the intruder mouse which was then immediately released into the isolated mouse's home cage. The TFT was recorded during the 3 minute test. Due to the lack of homogeneity of variance in the raw data, log-transformation was performed to normalize the variance prior to analysis of the data by one-way analysis of variance with subsequent Dunnett's comparison to control test ($p \leq 0.05$). A minimally effective dose (MED) was determined to be the lowest dose which produced a mean TFT significantly less than that of the control group. For the purposes of graphical representation, the data were expressed as mean percent of control.

In order to differentiate between specific antiaggressive effects and possible animal debilitation, rotorod motor coordination tests were conducted according to a modification of the procedures of Dunham and Miya [J. Am. Pharm. Assoc. 46, 208-209 (1957)] and Maj et al. [J. Neurol. Transm. 70, 1-17 (1987)]. Group-housed mice (20-25 g) were prescreened for their stability on a rotating rod (rotorod; 20 rpm) with 6 individual runs (Treadmill for mice, Ugo Basile, Varese, Italy). Only mice which could remain on the rotorod for 60 seconds in the last of 3 trials were used in subsequent testing. Test compound or vehicle was administered IP 60 minutes prior to testing (N=5-20/dose). The mice were placed on the rotorod, and the amount of time spent on the rotorod (maximum of 60 seconds) was recorded. One-way ANOVA with subsequent Dunnett's comparison to control tests ($p \leq 0.05$) was performed on the data. A MED was determined to be the lowest dose which produced an average time spent on the rotorod that was significantly less than that of the control group.

3. Ethanol Consumption

Sixty naive male Wistar rats (Charles River Canada, 175-225 g) were housed individually in stainless steel cages at 22° C. with free access to water and Purina Laboratory Rodent Chow. A 12 hour light/dark cycle was programmed with darkness commencing at 1900 hr. After +8 hours, an additional drinking tube containing 2% ethanol in distilled water was provided for each cage and the rats had a free choice between water and aqueous ethanol for 3 days. The drinking tube positions were switched daily. The ethanol concentration was increased by 1% every 3 days until a concentration of 5% was reached. All rats were weighed daily and water or aqueous ethanol intake recorded.

After 3 days at the 5% ethanol concentration the rats that had consumed the 5% ethanol consistently began baseline and the inconsistent or poor drinkers were dropped from the study. A total of 30 rats began baseline studies. Baseline consisted of 8 days of free choice between water and 5% aqueous ethanol. During this time each rat received intraperitoneal injections of Ringer's solution (NaCl, 0.86 g; KCl, 0.03 g; and $CaCl_2.2H_2O$, 0.033 g diluted to 100 ml with distilled water). Weight and water or 5% aqueous ethanol consumption were determined daily at 0800 hr and 1800 hr.

When baseline was completed the subjects were blocked into groups of five rats based on their g/kg ethanol consumption and began receiving treatment (zalopirone, 40 mg/kg; fluoxetine, 10 mg/kg or Ringer's solution as intraperitoneal injections. The treatment and control rats received treatment for two consecutive days followed by two consecutive days of washout with Ringer's solution. Throughout the treatment/washout period (20 days), the rats were given free access to water or 5% aqueous ethanol. Statistical analysis of data recorded in the post hoc Student-Newman-Keuls tests showed that during the treatment periods, fluoxetine and zalospirone-treated rats consumed significantly less ethanol when compared to control (Ringer's solution) on a g/kg or ml/rat basis. The total fluid intake of rats treated with zalospirone or fluoxetine was less than with the control animals with no significant differences in water consumption by treated vs. control rats. Rats receiving zalospirone and fluoxetine had significantly less weight gain and decreased food consumption compared to control rats.

Pharmaceutical Composition

The compounds of Formula I as exemplified by zalospirone, a $5-HT_{1A}$ modulating agent with anxiolytic properties, can thus be used in the treatment of alcoholism, sleep disorders, and aggressive behavioral symptoms of Alzheimer's disease.

The effective dosage of the active substances for such treatment will vary according to the particular compound being employed, and the severity and nature of the condition being treated. Therapy should be initiated at lower doses, the dosage thereafter being increased, if necessary, to produce the desired effect. In general, the compounds of the invention are most desirably administered at a concentration that will generally afford effective results without causing any harmful or delecterious side effects.

The compounds of formula (I) can be formulated into oral dosage forms such as tablets, capsules and the like. The compounds can be administered along or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be sufficient at least to impart the desired activity thereto on oral administration. The compounds may also be injected parenterally in which case they are used in the form of a sterile solution containing other solutes, for example, enough saline or glucose to make the solution isotonic.

What is claimed is:

1. A method of treating alcoholism, behavioral symptoms of Alzheimer's disease or sleep disorders which comprises administration to a mammal in need thereof a therapeutically effective amount of a compound having the formula:

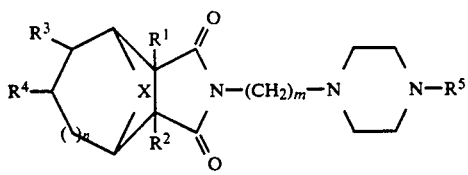

wherein:
n is 0–4;
m is 2–4;
$R^1$ and $R^2$ are H or $R^1$ and $R^2$ taken together forms a 3–5 membered carbocyclic ring;
$R^3$ and $R^4$ are H or $R^3$ and $R^4$ taken together form a 3–6 membered carbocylic ring;
with a proviso that when $R^1$, $R^2$, $R^3$ and $R^4$ are other than hydrogen, n is other than zero;
X is lower alkylene, vinylene or oxygen;
$R^5$ is unsubstituted or substituted phenyl, 2-pyridinyl, 2-pyrimidinyl, 2-pyrazinyl or 3-pyrazinyl where the substituents are selected from lower alkyl, lower alkoxy, halo, cyano, nitro and trifluoromethyl;
or a pharmaceutically acceptable salt thereof.

2. A method according to claim 1 wherein the compound used is a 3a, 4, 4a, 6a, 7a-hexahydro-2-[4-[4-(2-pyrimidinyl)-1-piperazinyl]butyl]-4,7-ethano-1H-cyclobut[f]isoindole-1,3(2H)dione.

* * * * *